(12) United States Patent
Krishnan et al.

(10) Patent No.: US 8,456,639 B2
(45) Date of Patent: Jun. 4, 2013

(54) MEASUREMENT OF CRITICAL DIMENSION

(75) Inventors: Shankar Krishnan, Santa Clara, CA (US); Haiming Wang, Fremont, CA (US)

(73) Assignee: KLA-Tencor Corporation, Milpitas, CA (US)

( * ) Notice: Subject to any disclaimer, the term of this patent is extended or adjusted under 35 U.S.C. 154(b) by 53 days.

(21) Appl. No.: 13/174,815

(22) Filed: Jul. 1, 2011

(65) Prior Publication Data

US 2013/0003068 A1    Jan. 3, 2013

(51) Int. Cl.
*G01N 21/55* (2006.01)
*G01N 21/00* (2006.01)

(52) U.S. Cl.
CPC ............... *G01N 21/55* (2013.01); *G01N 21/00* (2013.01)
USPC ...................... 356/445; 356/237.1; 356/237.2

(58) Field of Classification Search
CPC ............................... G01N 21/55; G01N 21/00
USPC ......................... 356/237.1–237.5, 445–448
See application file for complete search history.

(56) References Cited

U.S. PATENT DOCUMENTS

| | | | |
|---|---|---|---|
| 4,506,979 A | 3/1985 | Rogers | |
| 4,871,257 A * | 10/1989 | Suzuki et al. | 356/400 |
| 5,596,406 A | 1/1997 | Rosencwaig et al. | |
| 5,703,686 A | 12/1997 | Leroux | |
| 6,169,601 B1 | 1/2001 | Eremin et al. | |
| 6,654,131 B2 | 11/2003 | Opsal et al. | |
| 7,423,267 B2 * | 9/2008 | Nakasuji et al. | 250/310 |
| 7,483,133 B2 | 1/2009 | Bareket et al. | |
| 2008/0049233 A1 | 2/2008 | De Groot | |
| 2008/0129986 A1 | 6/2008 | Walsh | |
| 2008/0225282 A1* | 9/2008 | Chuang et al. | 356/237.4 |

* cited by examiner

*Primary Examiner* — Michael P Stafira
(74) *Attorney, Agent, or Firm* — Luedeka Neely Group, P.C.; Rick Barnes

(57) ABSTRACT

A spectroscopic instrument for conducting multi-wavelength, multi-azimuth, multi-angle-of-incidence readings on a substrate, the instrument having a broadband light source for producing an illumination beam, an objective for directing the illumination onto the substrate at multiple azimuth angles and multiple angels-of-incidence simultaneously, thereby producing a reflection beam, an aperture plate having an illumination aperture and a plurality of collection apertures formed therein for selectively passing portions of the reflection beam having desired discreet combinations of azimuth angle and angle-of-incident, a detector for receiving the discreet combinations of azimuth angle and angle-of-incident and producing readings, and a processor for interpreting the readings.

8 Claims, 2 Drawing Sheets

MEASUREMENT OF CRITICAL DIMENSION

FIELD

This invention relates to the field of integrated circuit fabrication. More particularly, this invention relates to multi-angle spectroscopic reflectometry as used in the metrology of integrated circuit structures.

INTRODUCTION

Spectroscopic tools, including both reflectometers and ellipsometers, have been widely used in the metrology and process control of integrated circuit fabrication processes. As the term is used herein, "integrated circuit" includes devices such as those formed on monolithic semiconducting substrates, such as those formed of group IV materials like silicon or germanium, or group III-V compounds like gallium arsenide, or mixtures of such materials. The term includes all types of devices formed, such as memory and logic, and all designs of such devices, such as MOS and bipolar. The term also comprehends applications such as flat panel displays, solar cells, and charge coupled devices.

Spectroscopic tools have been used, for example, to measure the thicknesses and critical dimension of samples such as film stacks and circuit structures. The measurements taken by these tools are based on measuring the diffraction of light through the material and geometric structures of the sample. Thus, as the dimensions of these structures become smaller (such as thickness and line width), the amount of diffraction that they create becomes very small. Therefore, it has become more difficult to measure these smaller structures and, at the same time, maintain the desired measurement precision and tool-to-tool uniformity.

Modern spectroscopic tools try to overcome these issues by measuring a sample at multiple wavelengths and multiple discrete angles. However, because at least one of the available wavelengths or the available angles are limited, it is difficult to set the wavelengths and measurement angles at values that produce the optimum measurement sensitivity as determined by a model-based analysis, given the fact that this optimum combination of wavelength and angle varies from sample to sample.

What is needed, therefore, is a system that reduces problems such as those described above, at least in part.

SUMMARY OF THE CLAIMS

The above and other needs are met by a spectroscopic instrument for conducting multi-wavelength, multi-azimuth, multi-angle-of-incidence readings on a substrate, the instrument having a broadband light source for producing an illumination beam, an objective for directing the illumination onto the substrate at multiple azimuth angles and multiple angels-of-incidence simultaneously, thereby producing a reflection beam, an aperture plate having an illumination aperture and a plurality of collection apertures formed therein for selectively passing portions of the reflection beam having desired discreet combinations of azimuth angle and angle-of-incident, a detector for receiving the discreet combinations of azimuth angle and angle-of-incident and producing readings, and a processor for interpreting the readings.

In this manner, the instrument is able to quickly take several readings at a desired combination of wavelengths, azimuth angles, and angles-of-incidence, simultaneously if desired. Thus, the aperture plates can be set up to capture the set of readings that is most sensitive to the substrate being measured, thereby increasing the accuracy of measurement. Further, the instrument can be quickly reconfigured for different readings on different substrates.

In various embodiments, the aperture plate is a set of aperture plates that can be used either individually or in combination to select different discreet combinations of multiple azimuth angles and multiple angles-of-incident. In other embodiments, the aperture plate is electronically configurable to produce different discreet combinations of multiple azimuth angles and multiple angles-of-incident. In some embodiments, the detector receives the discreet combinations of azimuth angle and angle-of-incident simultaneously. In other embodiments, the detector receives the discreet combinations of azimuth angle and angle-of-incident serially.

BRIEF DESCRIPTION OF THE DRAWINGS

Further advantages of the invention are apparent by reference to the detailed description when considered in conjunction with the figures, which are not to scale so as to more clearly show the details, wherein like reference numbers indicate like elements throughout the several views, and wherein.

DETAILED DESCRIPTION

Various embodiments of the present invention describe a spectroscopic tool (reflectometer or ellipsometer) that can measure a sample at any continuously-variable composite angle within the entire half-hemisphere (angle of incidence of from about zero to about ninety degrees, azimuth angle of from −180 to 180 degrees, with respect to the measurement spot in the plane of the sample), and at more than one composite angle simultaneously or sequentially, where composite angle refers to the combination of incidence and azimuth.

These embodiments conduct measurements at each of the angles corresponding to a small collection aperture, which removes the integration of multiple rays in model-based analysis, leading to significant improvements in measurement speed and throughput, while maintaining the small measurement spot that is desired in integrated circuit fabrication processes.

Figure 1:
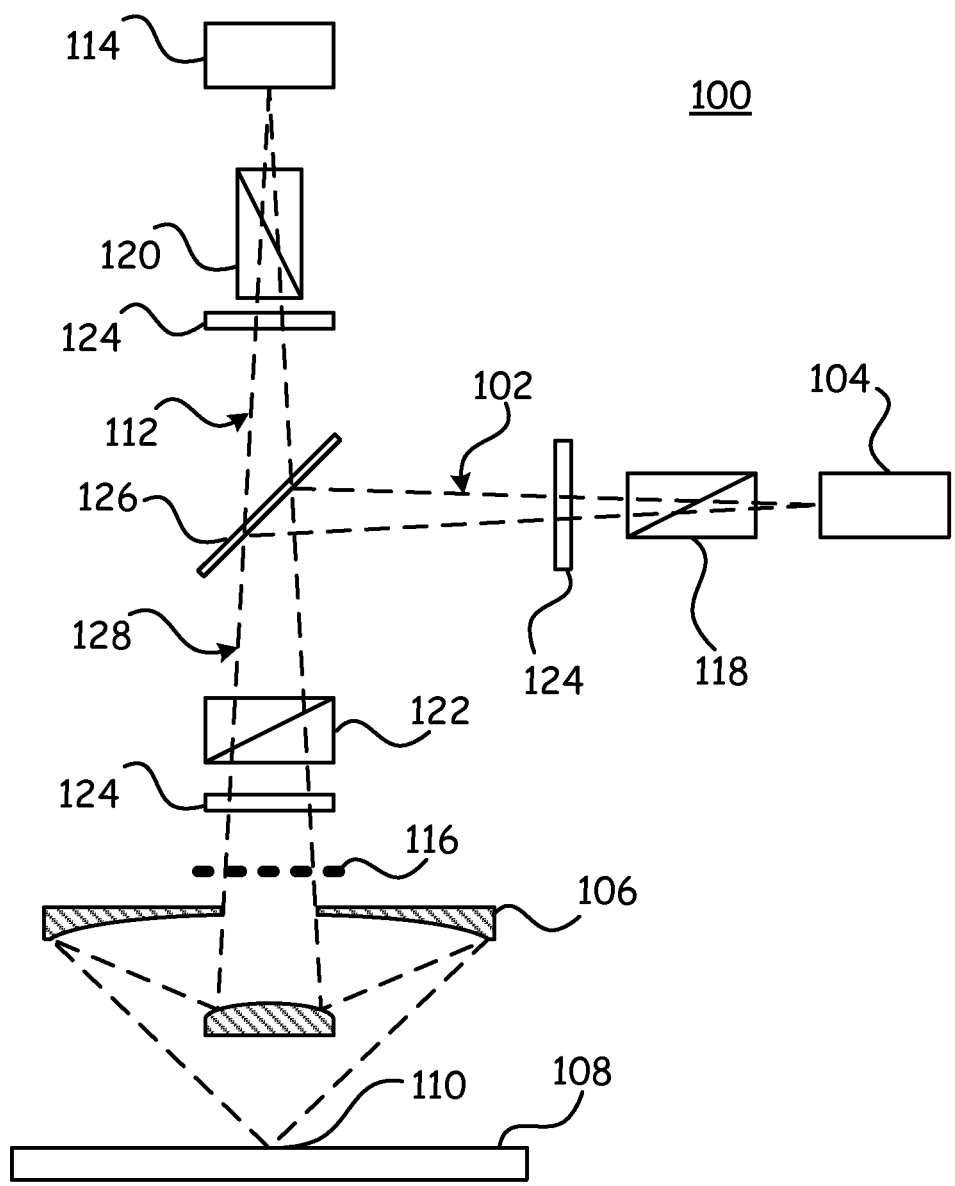
FIG. 1 depicts a composited multi-angle spectroscopic tool according to multiple embodiments of the present invention.

With reference now to FIG. 1, there is depicted a multi-angle spectroscopic tool 100 according to several composited embodiments of the present invention. Thus, any given embodiment might not have all of the structures depicted in FIG. 1. Instead, FIG. 1 depicts the various essential and optional elements that could be present in the different embodiments.

Light 102 from a broadband light source 104 is directed to an objective lens 106 to illuminate the sample 108 at spot 110. A two-lens objective 106 is depicted in FIG. 1, but other objective lens 106 designs are also contemplated. The objective lens 106 illuminates the sample 108 from substantially any continuously-variable composite angle with a cone of light. The light 112 that is reflected from the sample 108 is collected by the objective 106, and directed to a spectrometer 114 for measurement. A beam splitter 126 allows the light paths 102 and 112 to be along a common path 128 between the beam splitter 126 and the sample 108.

A polarizer 118 is optionally placed in the illumination path 102 in some embodiments, enabling polarized spectroscopic reflectometry measurements, in which the polarization state in the collection path 112 is determined by the angular position of the plane of incidence in reference to the illumination polarization state. To explicitly define the polarization state in the collection path 112, another polarizer, referred to as the analyzer 120, is optionally placed in the collection path 112. In alternate embodiments, a single polarizer 122 is placed in the common path 128, in place of the polarizer 118 and the analyzer 120, in a so-called double-pass configuration. Other embodiments include a waveplate 124 disposed in one or both of the illumination path 102 and the collection path 112, or alternately in the common path 128. These elements 118, 120, 122, and 124 can either be fixed or rotating, in virtually any combination.

Figure 2:
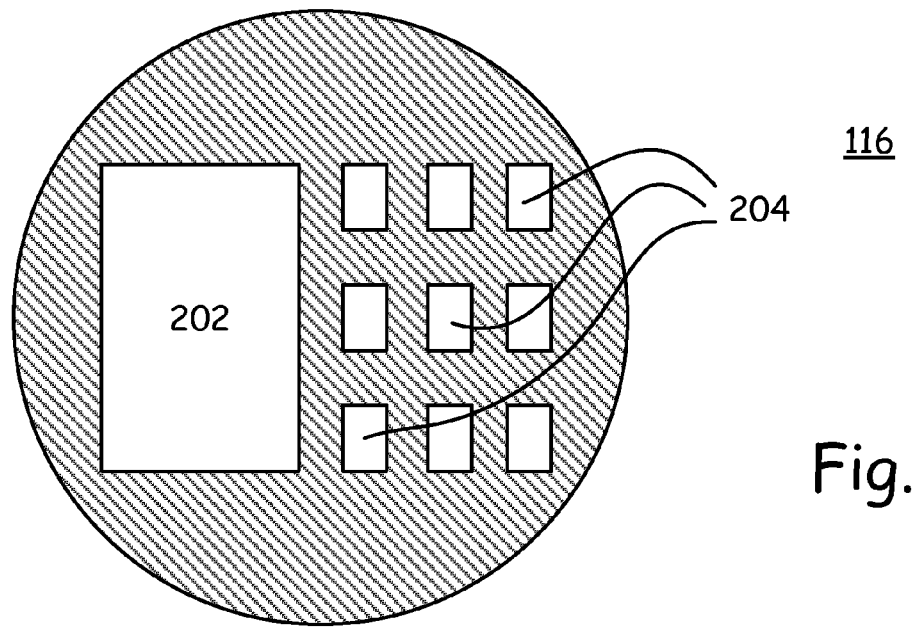
FIG. 2 depicts an aperture plate according to a first embodiment of the present invention.
Figure 3:
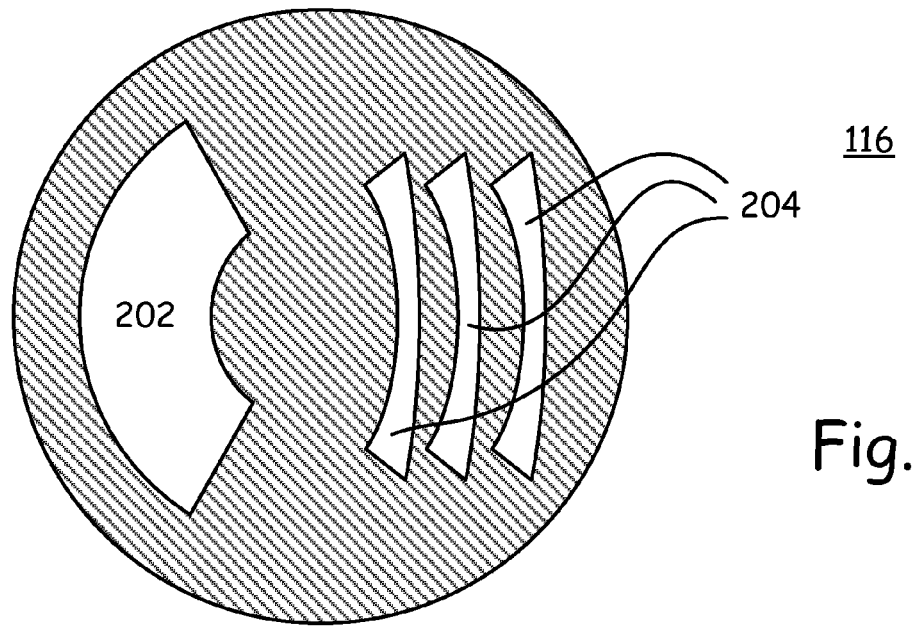
FIG. 3 depicts an aperture plate according to a second embodiment of the present invention.

An aperture plate 116 selectively blocks and transmits the desired fan of both illumination light 102 and reflected light 112. In some embodiments, the aperture plate 116 is disposed either adjacent or within the aperture in the objective 106. Embodiments of the aperture plate 116 are depicted in greater detail in FIGS. 2 and 3. FIG. 2 depicts an illumination aperture 202 that passes desired portions of the illumination beam 102 (as a component of the composite beam 128) and collection apertures 204 disposed in rows and columns in the aperture plate 116 that pass desired portions of the reflection beam 112 (as a component of the composite beam 128). Points within the collection apertures 204 that lie along a circle that is concentric with the axis of the reflection beam 112 all have substantially identical angles of incidence. Points within the collection apertures 204 that lie along a common radial line extending out from the axis of the reflection beam 112 all have substantially identical azimuth angles. The collection apertures 204 can be fashioned with both illumination apertures 202 and collection apertures 204 configured so as to simultaneously receive with at sensor 114 a plurality of broadband readings from a plurality of azimuth angles and angles of incidence. By fashioning the collection apertures 204 as very small openings, the integration of rays from too broad a fan can be removed from the model-based analysis, thus leading to significant improvements in measurement speed and throughput, while maintaining the small measurement spot required in integrated circuit fabrication processes. The numbers and sizes of the apertures 204 are by way of example only.

In some embodiments, the film stack to be analyzed by the tool 100 is mathematically modeled prior to measurement, and it is determined which composite angle or set of composite angles offers the greatest sensitivity. An aperture plate 116 is then fabricated with collection apertures 204 specifically located for this set of composite angles (for example), where the different composite angles in the set are either serially selectable, as depicted in the example of the aperture plate 116 of FIG. 2, or are simultaneously investigated, as depicted in the example of the aperture plate 116 of FIG. 3. Additional standard collection apertures 204 could also be added to such custom aperture plates 116, so that the aperture plate 116 could be used for generic measurements.

Different aperture plates 116 can be fabricated as optimized for different film stacks, and then swapped out of the tool 100 as desired. In other embodiments the collection apertures 204 of the aperture plate 116 are configurable such as by processor-driven motorized mechanical or electronic shuttering means (such as a liquid crystal panel) that can be reconfigured as to the number, size, and placement of the collection apertures 204 in the aperture plate 116.

Different embodiments use various means to receive, either sequentially or simultaneously, the reflected light 112 from the different composite angles. Various embodiments of these means are described below.

Option 1: Select one composite angle at a time using an aperture plate 116 configured to do such, and the spectrometer 114 produces a signal from the light 112 gathered from this composite angle only. Accessing additional composite angles is conducted sequentially thereafter by moving or replacing the aperture plate 116.

Option 2: Select multiple angles (such as three angles) at the same time with an aperture plate 116 configured to do such, use optics to shift the multiple reflection beams 112 into different parts of the spectrometer 114, which detects the signals simultaneously.

Option 3: Select multiple angles (such as four) at the same time with an aperture plate 116 configured to do such, use optics to shift the multiple reflection beams 112 into multiple spectrometers 114 (such as four, to continue the example) to detect the signals corresponding to the multiple composite angles simultaneously.

Option 4: Use optics, such as micro-electronic-mechanical system minors, to partition the beam 112 or direct selected portions of the beam 112 through the aperture plate 116.

The foregoing description of embodiments for this invention has been presented for purposes of illustration and description. It is not intended to be exhaustive or to limit the invention to the precise form disclosed. Obvious modifications or variations are possible in light of the above teachings. The embodiments are chosen and described in an effort to provide illustrations of the principles of the invention and its practical application, and to thereby enable one of ordinary skill in the art to utilize the invention in various embodiments and with various modifications as are suited to the particular use contemplated. All such modifications and variations are within the scope of the invention as determined by the appended claims when interpreted in accordance with the breadth to which they are fairly, legally, and equitably entitled.

What is claimed is:

1. A spectroscopic instrument for conducting multi-wavelength, multi-azimuth, multi-angle-of-incidence readings on a substrate, comprising:
   a broadband light source for producing an illumination beam along a composite beam pathway,
   an objective for directing the illumination beam onto the substrate at multiple azimuth angles and multiple angels-of-incidence simultaneously, thereby producing a reflection beam along the composite bean pathway,
   an aperture plate having an illumination aperture and a plurality of collection apertures formed therein, for selectively passing first portions of the illumination beam and second portions of the reflection beam having desired discreet combinations of azimuth angle and angle-of-incident, wherein the first portions and the second portions are separate portions of the combined beam pathway,
   a detector for receiving the discreet combinations of azimuth angle and angle-of-incident and producing readings, and
   a processor for interpreting the readings.

2. The spectroscopic instrument of claim 1, wherein the aperture plate comprises a set of aperture plates that can be used either individually or in combination to select different discreet combinations of multiple azimuth angles and multiple angles-of-incident.

3. The spectroscopic instrument of claim 1, wherein the aperture plate is electronically configurable to produce different discreet combinations of multiple azimuth angles and multiple angles-of-incident.

4. The spectroscopic instrument of claim 1, wherein the detector receives the discreet combinations of azimuth angle and angle-of-incident simultaneously.

5. The spectroscopic instrument of claim 1, wherein the detector receives the discreet combinations of azimuth angle and angle-of-incident serially.

6. The spectroscopic instrument of claim 1, wherein the spectroscopic instrument is a reflectometer.

7. The spectroscopic instrument of claim 1, wherein the spectroscopic instrument is an ellipsometer.

8. The spectroscopic instrument of claim 1, wherein the objective is adjustable to direct the illumination beam at all azimuth angles and substantially all angles-of-incidence.

* * * * *

UNITED STATES PATENT AND TRADEMARK OFFICE
CERTIFICATE OF CORRECTION

| | | |
|---|---|---|
| PATENT NO. | : 8,456,639 B2 | Page 1 of 1 |
| APPLICATION NO. | : 13/174815 | |
| DATED | : June 4, 2013 | |
| INVENTOR(S) | : Krishnan et al. | |

It is certified that error appears in the above-identified patent and that said Letters Patent is hereby corrected as shown below:

Title Page, Item (57) Abstract, line 6, "angels-of-incidence" should read --angles-of-incidence--.

Title Page, Item (57) Abstract, lines 11-12, "discreet" should read --discrete--.

In the Specification

Column 1, line 55, "angels-of-incidence" should read --angles-of-incidence--.

Column 1, lines 59 and 60, "discreet" should read --discrete--.

Column 2, lines 6, 9, 11, and 13, "discreet" should read --discrete--.

In the Claims

Column 4, Claim 1, line 49, "angels-of-incidence" should read --angles-of-incidence--.

Column 4, Claim 1, lines 55 and 59, "discreet" should read --discrete--.

Column 4, Claim 2, line 66, "discreet" should read --discrete--.

Column 5, Claim 3, line 3, "discreet" should read --discrete--.

Column 5, Claim 4, line 6, "discreet" should read --discrete--.

Column 5, Claim 5, line 9, "discreet" should read --discrete--.

Signed and Sealed this
Twenty-ninth Day of October, 2013

Teresa Stanek Rea
*Deputy Director of the United States Patent and Trademark Office*